United States Patent
Quintero Osorio et al.

(10) Patent No.: US 11,925,758 B2
(45) Date of Patent: Mar. 12, 2024

(54) ROTARY OCCLUSION VALVE FOR TRACHEOSTOMY

(71) Applicants: Fundación Valle de Lili, Cali (CO); Oscar Ivan Quintero Osorio, Cali (CO)

(72) Inventors: Oscar Ivan Quintero Osorio, Cali (CO); Diana Marcela Osorio, Cali (CO)

(73) Assignee: Fundación Valle De Lili, Cali (CO)

( * ) Notice: Subject to any disclaimer, the term of this patent is extended or adjusted under 35 U.S.C. 154(b) by 652 days.

(21) Appl. No.: 17/266,917

(22) PCT Filed: Aug. 8, 2019

(86) PCT No.: PCT/IB2019/056769
§ 371 (c)(1),
(2) Date: Feb. 8, 2021

(87) PCT Pub. No.: WO2020/031137
PCT Pub. Date: Feb. 13, 2020

(65) Prior Publication Data
US 2021/0338956 A1    Nov. 4, 2021

(30) Foreign Application Priority Data

Aug. 8, 2018    (CO) .................. NC2018/0008335

(51) Int. Cl.
*A61M 16/04* (2006.01)
*A61M 16/20* (2006.01)
(Continued)

(52) U.S. Cl.
CPC ...... *A61M 16/0468* (2013.01); *A61M 16/208* (2013.01); *F16K 15/148* (2013.01); *F16K 15/1825* (2021.08)

(58) Field of Classification Search
CPC ............ A61M 16/0468; A61M 16/208; A61M 16/1005; A61M 16/0833; A61M 16/047;
(Continued)

(56) References Cited

U.S. PATENT DOCUMENTS

| 4,538,607 A | 9/1985 | Saul |
| 8,800,565 B1* | 8/2014 | Root ................. A61M 16/0468 |
| | | 128/207.15 |

(Continued)

FOREIGN PATENT DOCUMENTS

| CA | 2347190 A1 | 4/2000 |
| CA | 2814204 A1 | 4/2012 |

OTHER PUBLICATIONS

International Application No. PCT/IB2019/056769, International Search Report dated Nov. 4, 2019, ISA/INAPI; 4 pp.

(Continued)

*Primary Examiner* — Michael R Reid
*Assistant Examiner* — Tina Zhang
(74) *Attorney, Agent, or Firm* — Resonance IP Law, PC

(57) ABSTRACT

A rotary occlusion valve for tracheotomy is described, used in the medical field, which allows the function of occluding the flow, both inspiratory and expiratory, of a particular patient, depending on his or her clinical condition or ventilatory limitations, thus permitting the execution of the two steps of respiration, inspiration and expiration. The valve consists in a device composed of a main body in the form of a cylinder inside which is a bearing, a safety grille, a tab, and an oxygen connection port. Said main body is joined to a rotary one-way valve containing a spherical ball, an orifice in its center, windows, pillars, and a tab. Finally, the one-way valve contains a membrane consisting of a grip port and a diaphragm.

5 Claims, 10 Drawing Sheets

(51) Int. Cl.
    *F16K 15/18*     (2006.01)
    *F16K 15/14*     (2006.01)

(58) Field of Classification Search
    CPC .... A61M 16/209; F16K 15/14; F16K 15/148; F16K 15/1825; Y10T 137/5153
    USPC ..................................................... 137/269.5
    See application file for complete search history.

(56) References Cited

U.S. PATENT DOCUMENTS

| | | | |
|---|---|---|---|
| 9,981,100 B2 | 5/2018 | Bare et al. | |
| 10,641,403 B2 * | 5/2020 | Maxfield | F16K 31/52425 |
| 2007/0251523 A1 | 11/2007 | Landuyt | |

OTHER PUBLICATIONS

International Application No. PCT/IB2019/056769, Written Opinion dated Nov. 4, 2019, ISA/INAPI; 7 pp.
Prigent, H., et al., Characteristics of tracheostomy phonation valves. European Respiratory Journal, vol. 27, No. 5, 2006, pp. 992-996.

* cited by examiner

ROTARY OCCLUSION VALVE FOR TRACHEOSTOMY

BACKGROUND OF THE INVENTION

In general, tracheotomy phonation valves used in patients who have been subjected to an artificial airway system or tracheotomy cannula and whose stable medical conditions allow initiating the process of removing the cannula by means of functional rehabilitation, in view of various special circumstances in the upper airways[1], are unidirectional valves that only allow a partial occlusion, i.e., they allow only one respiratory stage, either inspiration or expiration.

These one-way valves are generally tolerated by patients, although in some cases rejection to treatment may occur, such as when there is an increased ventilatory flow due to coughing episodes, which are accompanied by reduced tracheal lumen. In this case correct air passage is impeded, increasing intrapulmonary pressure and causing the expulsion of the valve.

However, there is a different group of patients that present a poor coughing pattern due to extended hospitalization, muscular weakness, neuromuscular disorders, etc. which, when using one-way valves, cause the secretions to rise to the oropharynx, which in some cases renders the valves ineffective and leads to the patient's intolerance to treatment.

The oronasal product of US patent US 2012/0103342 A1 describes a valve having a one-way ball design that presents a decreased resistance to air flow. In this regard, when the orientation of the valve is changed in the internal cannula, tracheotomy patients can adjust the flow and sealing characteristics to achieve an optimum respiration and speech configuration, also including a retaining cord for connection to the tracheotomy tube to prevent losing the valve. Accordingly, the patent discloses a phonation tube for managing the patient's airway having a body with a chamber formed in its interior connected to a tracheotomy tube. There is also a plurality of ramps arranged inside the chamber that retain a ball in the chamber. The body can rotate 180° to adjust the position of the ball when the patient inspires and expires, thereby aiding speech, while the heat and humidity exchanger can be joined to the body.

This invention differs from the one proposed in the application in that the mechanism of operation takes place through a ball or sphere, while the "rotary occlusion valve" works by means of a membrane. In addition, when there is a large increase in ventilatory flow, such as during coughing episodes in patients with upper airway obstruction, the "rotary occlusion valve" allows the complete exit of air through the valve, preventing its expulsion, while in the aforementioned patent the valve could be expelled. Moreover, the oronasal product does not have an oxygen connection port.

Also known is the "TRACH VOX" product, which involves a valve with a spring that can be hermetically closed with the fingers during speech, so that when the fingers are removed the valve automatically opens. This product has an integrated suction port that acts as a relief valve while a patient is coughing and an integrated oxygen connector. It differs from the present application in that the "rotary occlusion valve" guarantees a full seal during air passage through the tracheotomy in both the inspiration and expiration processes. This allows a more objective recovery by promoting the rise of the secretions towards the oropharynx or, in patients who need to expire through the tracheotomy, for the air outlet can be performed without limitations and in an easier way.

Similarly, document U.S. Pat. No. 4,538,607 provides an adjustable two-way tracheotomy valve for both inspiration and expiration, in which case it can also be used as a phonation valve. The valve comprises three main elements: a cylindrical casing, a complementary lid, and a disc-shaped element placed inside said casing and lid for displacing turpentine. The lid has a circular end with an off-center opening that defines an air inlet/outlet or only an inlet, depending on the position of the lid. Said patent differs from the present application in that it does not only allow a single direction of occlusion if necessary, and in that it does not have an oxygen connection port nor a safety grille.

On the other hand, document EP1025874A1 discloses a valve with a housing that contains a pivoting flap that adopts a sealing position against the open lumen when sufficient inspiration force is applied, and moves away from said lumen when sufficient expiration force is applied. The valve includes a shunting accessory through which it is possible to inspire when the tracheotomy valve is closed. The points at which this flap adopts an open or closed position are adjustable. This device provides its greatest benefits in the case of high ventilatory flow. It has a relief valve that opens in response to a high pressure, such as when there is a coughing episode, but which differs from the present application in that it does not provide the full occlusion in one ventilatory direction when required, does not have a grille, and does not have an oxygen connection.

In conclusion, the rotary occlusion tracheotomy valve proposed by the present application allows a single device to provide the two occlusion options for the ventilatory flow in a patient, depending on the patient's medical condition and personal needs. Consequently, the present invention is characterized by facilitating inspiration and limiting expiration through the tracheotomy and, when turning it 180°, generating the opposite effect, facilitating expiration and limiting inspiration through the tracheotomy.

In this sense, when the one-way valve of the "rotary occlusion valve for tracheotomy" is used, facilitating inspiration and occluding expiration through the tracheotomy, the ventilatory flow is directed towards the oropharynx, allowing the patient to speak, cough, and expel secretions physiologically through the oropharynx. Instead, when the rotary occlusion valve for tracheotomy is used to occlude inspiration and favor expiration through the tracheotomy, the patient receives the functional rehabilitation meant to again perform inspiration through the upper airway, allowing the air that reaches the lungs to be modified so that it passes through the nasal cavity, which filters, warms, and humidifies the ambient air.

Moreover, in situations of cough episodes with reduced tracheal lumen, the valve allows an adequate air outlet through the tracheotomy. In this situation, if the patient wishes to speak it is enough to press a finger on the valve, directing the airflow to the vocal cords, preventing contamination due to direct contact of the finger on the tracheotomy cannula. Thus, when the patient has regained increased tracheal lumen and/or increased respiratory strength, the occlusion system can be inverted by rotating the one-way valve by 180° and subsequently obtaining 100% occlusion with the plugs available in tracheotomy kits.

FIELD OF THE ART

The present invention belongs to the field of medical science, in particular devices specially adapted for medical use, such as respiratory valves.

BRIEF DESCRIPTION OF THE INVENTION

A rotary occlusion valve for tracheotomy is described, used in the medical field, which allows the function of occluding the flow, both inspiratory and expiratory, of a particular patient, depending on his or her clinical condition or ventilatory limitations, thus permitting the execution of the two steps of respiration, inspiration and expiration. The valve consists in a device composed of a main body in the form of a cylinder inside which is a bearing, a safety grille, a tab, and an oxygen connection port. Said main body is joined to a rotary one-way valve containing a spherical ball, an orifice in its center, windows, pillars, and a tab. Finally, the one-way valve contains a membrane consisting of a grip port and a diaphragm.

DESCRIPTION OF THE DRAWINGS

To further explain the invention, the following set of drawings is provided, for illustrative purposes only, which include, but are not limited to, the following.

DETAILED DESCRIPTION OF THE INVENTION

The rotary occlusion valve for tracheotomy (1) proposed by the invention has been designed as a novel device that allows enhancing the functional rehabilitation of tracheotomy patients in their transition from spontaneous respiration to full occlusion of the tracheotomy cannula, particularly in cases where there is a limited respiratory flow due to alterations in the airway, or a poor cough pattern associated with weakness of the respiratory muscles.

Figure 1:
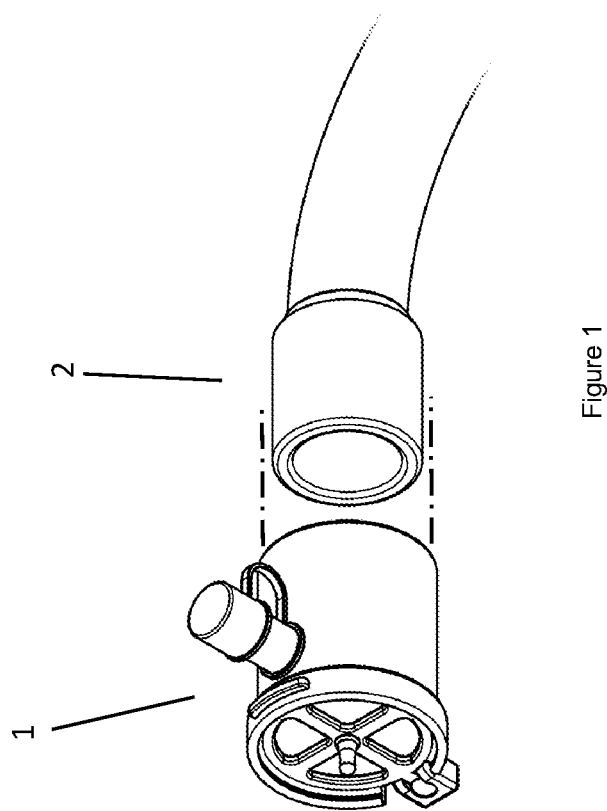
FIG. 1: Shows the rotary occlusion valve for tracheotomy (1), separated from a tracheotomy cannula (2).
Figure 3:
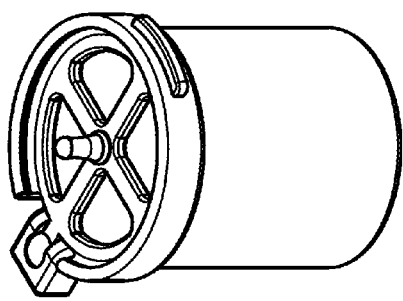
FIG. 3: Shows the isometric design of the rotary occlusion valve for tracheotomy without a port for connecting oxygen.
Figure 2:
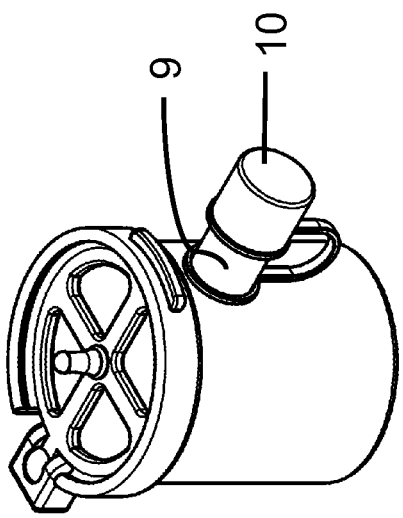
FIG. 2: Shows the isometric design of the rotary occlusion valve for tracheotomy with a port for connecting oxygen.

FIG. 1 shows the rotary occlusion valve for tracheotomy (1), separated from a tracheotomy cannula (2). This valve can have an oxygen connection port (9), as shown in FIG. 2, or lack such a port, as shown in FIG. 3, according to one of its embodiments.

Thus, the rotary occlusion valve for tracheotomy (1) comprises three main components (FIG. 4): a main cylindrical body (3) and a rotary one-way valve (5) made from a rigid plastic material, and a one-way membrane (4).

Figure 5:
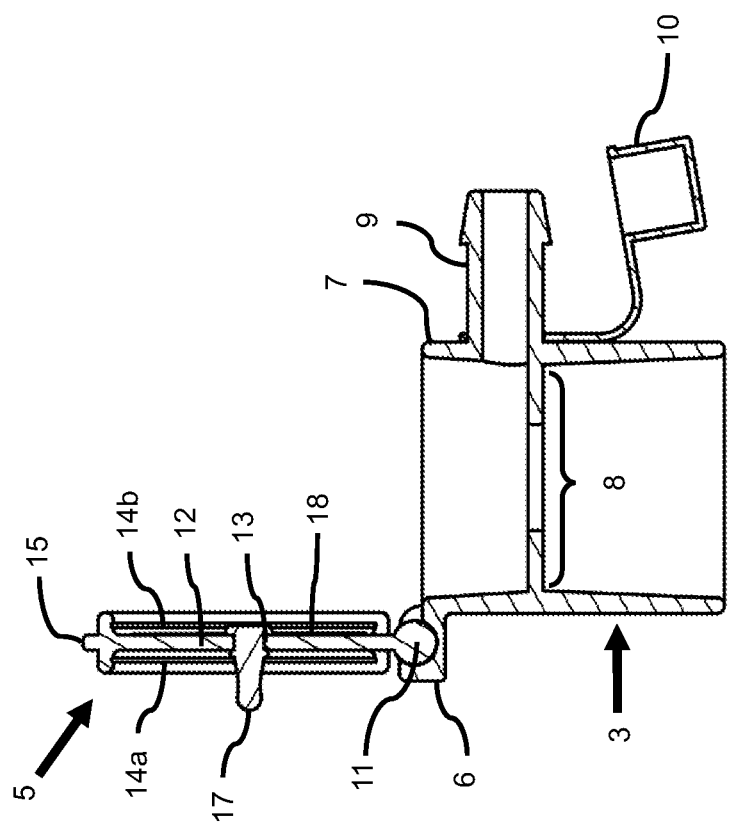
FIG. 5: Shows a lateral sagittal sectional view of the connected parts of the rotary occlusion valve for tracheotomy with a connection port for oxygen.
Figure 6:
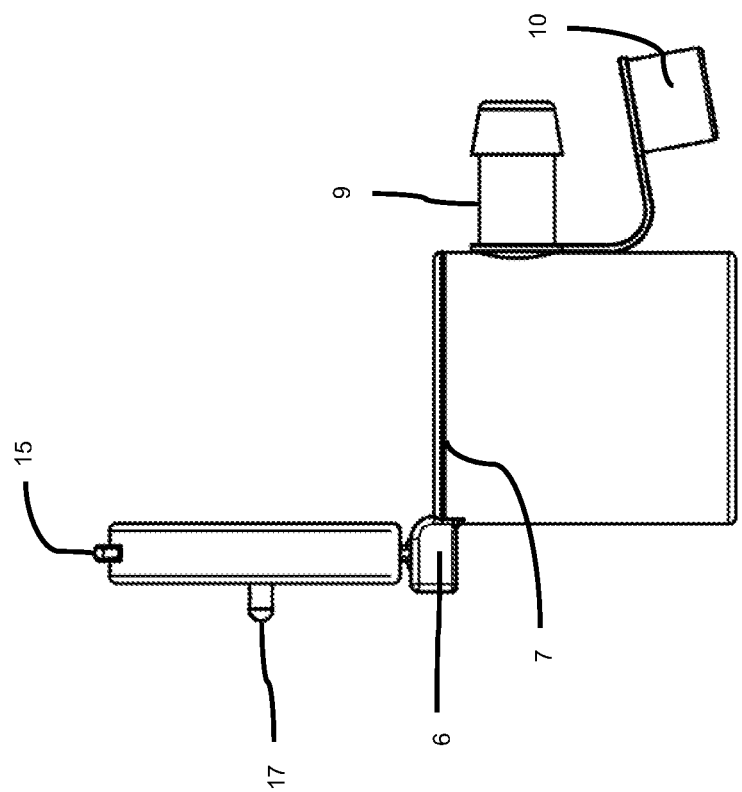
FIG. 6: Shows a side view of the isometric design of the rotary occlusion valve for tracheotomy with a port for connecting oxygen.
Figure 7:
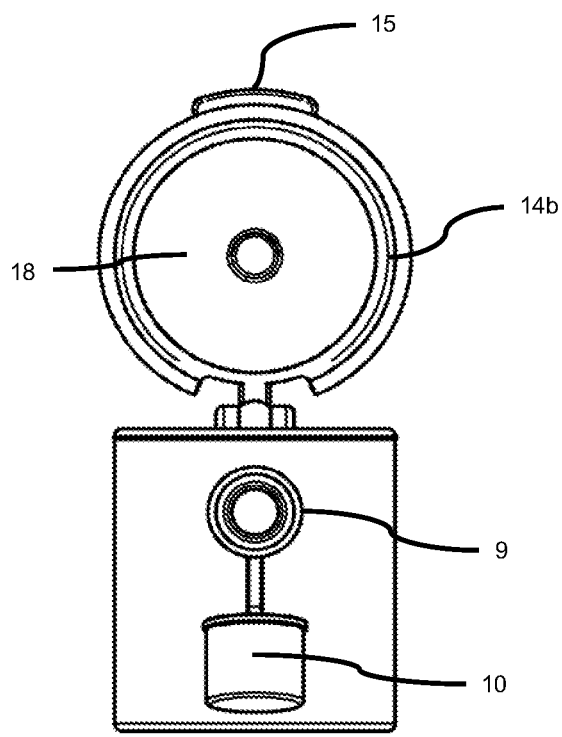
FIG. 7: Shows a front view of the isometric design of the rotary occlusion valve for tracheotomy with the port for connecting oxygen.
Figure 8:
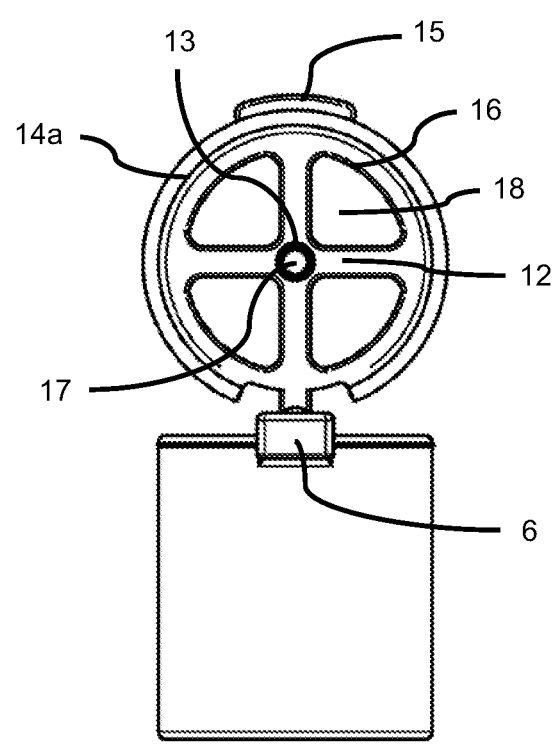
FIG. 8: Shows a rear view of the isometric design of the rotary occlusion valve for tracheotomy with a port for connecting oxygen.
Figure 9:
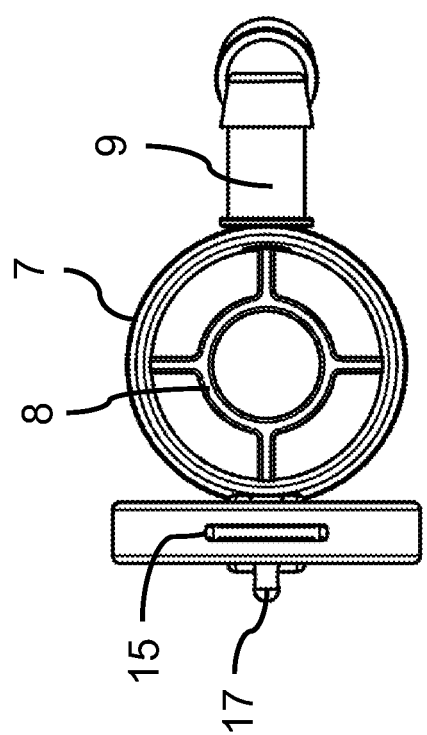
FIG. 9: Shows a top view of the isometric design of the rotary occlusion valve for tracheotomy with a port for connecting oxygen.
Figure 10:
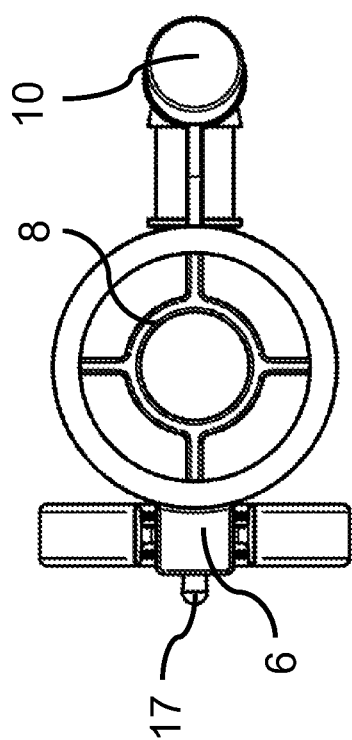
FIG. 10: Shows a bottom view of the isometric design of the rotary occlusion valve for tracheotomy with the port for connecting oxygen.
Figure 11:
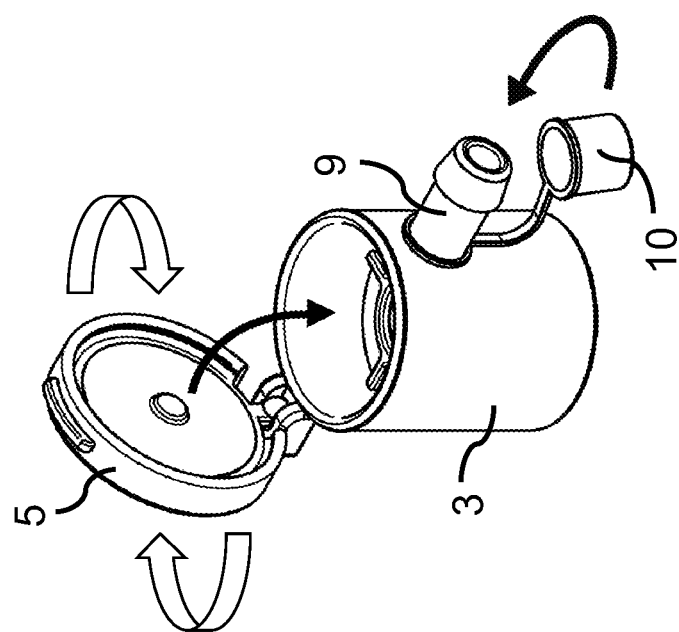
FIG. 11: Shows the isometric design of the rotary occlusion valve for tracheotomy with the 360° rotation mechanism of the one-way valve (5) and the closing direction against the main body (3). It also shows the closing direction of the lid (10) against the oxygen connection port (9).

These parts in turn have components as shown in FIG. 5. The main body (3) of the rotary occlusion valve for tracheotomy (1) has a bearing (6), a tab (7), a safety grille (8) and an oxygen connection port (9) with the corresponding lid (10), which may or may not be present in the invention (1). The one-way rotary valve (5) contains a spherical cap (11), pillars (12), a central orifice (13), a tab (15), window frames (16), an inner edge on the side of the gripping port (14a) and an inner side on the side opposite the gripping port (14b). Finally, the one-way membrane has a gripping port (17) and the diaphragm (18).

In accordance with the above, the one-way valve (5) by means of one of its inner edges (either the inner edge on the gripping port side (14a) or the inner edge on the opposite side (14b)), fits snugly on one of its two faces against the tab (7) of the anterior edge of the main body (3), and is also provided with a spherical cap (11) to allow it to move, mounted in the bearing (6) of the main body (3). It has window frames (16) that allow closing or opening air passage with the one-way membrane (4) fitted against the pillars (12) and are secured to the one-way valve (5) by being contained by a gripping port (17) that passes through the central orifice (13) of the one-way valve (5). It also has a tab (15) that simplifies removal from the tab (7) of the main body (3).

If the oxygen connection port (9) is present, as shown in FIGS. 1, 2, 6, 7, 8, 9, 10 and 11, it is housed on the lateral part of the main body from which it protrudes, remaining closed by a lid (10) and, if needed, allows the connection of hoses for supplying oxygen to the patient after lifting said lid (10).

Figure 4:
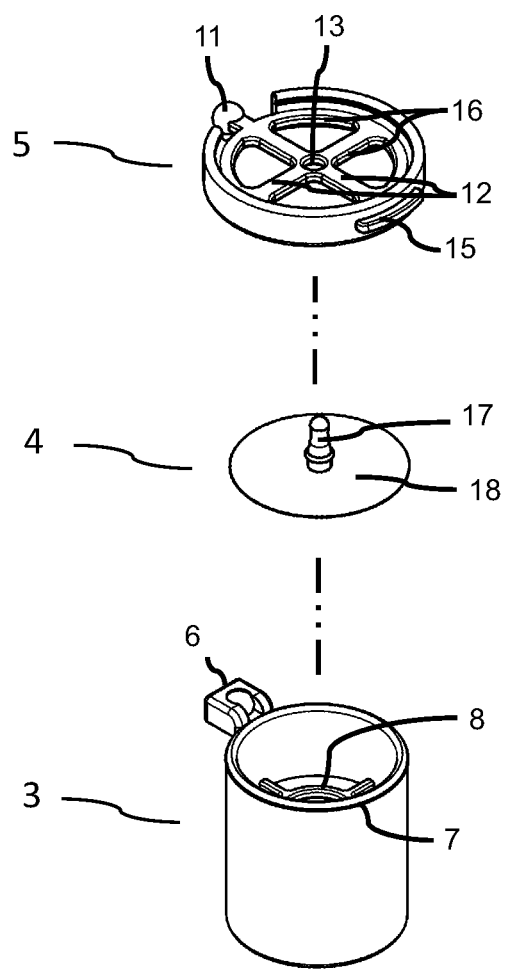
FIG. 4: Shows the isometric design of the rotary occlusion valve for tracheotomy without the port for connecting oxygen, separated into its main components: The main body (3), the one-way membrane (4) and the one-way valve (5).

As indicated above, in other embodiments the rotary occlusion valve for tracheotomy (1) may not have an oxygen connection port (9), as shown in FIGS. 3 and 4.

In this regard, the present invention is characterized by facilitating inspiration and limiting expiration through the tracheotomy and, when rotating it 180°, has the opposite effect, facilitating expiration and limiting inspiration through the tracheotomy.

Preferred Embodiment of the Invention

The functioning of the rotary occlusion valve for tracheotomy that constitutes the object of the invention is as follows:

The patient's clinical condition must first be evaluated to determine the respiratory limitation. In view of the above it may be necessary to occlude inspiration and facilitate expiration through the tracheotomy, or instead to occlude expiration and facilitate inspiration through the tracheotomy.

According to the above, to occlude inspiration and facilitate expiration through the tracheotomy the one-way valve (5) must be closed to adjust the inner edge on the side of the gripping port (14a) of the one-way valve against the tab (7) of the main body, so that the diaphragm (18) of the one-way membrane (4) is placed on the outer face of the rotary occlusion valve for tracheotomy and the gripping port (17) is on the inner face. Thus, when the patient inspires the diaphragm (18) is fitted against the pillars (12), preventing air passage through the windows (16) so that air enters the lungs through the upper airway. When expiring the air exits through the windows (16), lifting the diaphragm (18), facilitating a correct coughing pattern, particularly in patients with reduced tracheal lumen or poor coughing patterns. In this position it is possible to speak by closing the diaphragm (18) with the finger; if the patient requires oxygen, it is supplied through the upper airway with an oronasal mask or nasal cannula.

To produce the opposite effect, occluding expiration and favoring inspiration through the tracheotomy, the one-way valve (5) must be separated from the main body (3) by pulling on the tab (15), then rotating the one-way valve (5) 180° with the spherical cap (11) contained in the bearing (6), and again closing the one-way valve (5) such that the inner edge on the side opposite the gripping port (14b) is fitted against the tab (7) of the main body (3). In this way, the diaphragm (18) of the one-way valve (4) is placed on the inner face of the rotary occlusion valve for tracheotomy, and the gripping port (17) is on the outer face. Thus, when the patient inspires the air will pass through the windows (16) overcoming the resistance of the diaphragm (18), and when expiring phonation and coughing is facilitating by directing the air towards the upper airway. In this position if the patient requires oxygen the hose can be connected directly to the oxygen port (9) or to a tracheotomy mask. As an additional safety mechanism, the inner grille (8) acts as a containment system for the one-way valve (4), preventing bronchoaspiration in case of detachment if it is poorly fitted during routine cleaning and disinfection processes.

The rotary occlusion valve for tracheotomy proposed by the invention can be separated into its main components to aid in its cleaning.

The invention claimed is:

1. A rotary occlusion valve for tracheotomy comprising: a cylindrical main body (3) containing a one-way membrane (4) and connected to a rotary one-way valve (5), where the rotary one-way valve (5) is fitted on one of its two faces through one of its inner edges (14a or 14b) against a tab (7) of the anterior edge of the main body (3), and a spherical cap (11) enables a 180° rotary movement of the rotary one-way valve (5), as the spherical cap (11) is assembled in a bearing (6) of the main body (3), where in addition the rotary one-way valve (5) comprises window frames (16) that allow the closing or opening of an air passage through the one-way membrane (4) that is fitted against pillars (12) of the one-way valve (5) and is held in place by a gripping port (17) that passes through a central orifice (13) of the one-way valve (5).

2. The rotary occlusion valve for tracheotomy according to claim 1, characterized in that the main body (3) has a bearing (6) joined to the main body, the tab in the anterior edge (7) in which the one-way valve is fitted, an oxygen connection port (9) with a lid (10) and an internal safety grille (8) that acts as a containment system for the one-way membrane (4).

3. The rotary occlusion valve for tracheotomy according to claim 2 characterized in that the oxygen connection port (9) is placed on the lateral part of the main body (3) protruding from it and remaining closed with the lid (10) and, if oxygen supply is needed, allows the connection of hoses after lifting the lid (10).

4. The rotary occlusion valve for tracheotomy according to claim 1 characterized in that the rotary one-way valve (5) has the pillars (12) against which the one-way membrane (4) is fitted, the window frames (16) that can open or close the air passage, the central orifice (13) in which the gripping port (17) is fitted, the inner edge on the side of the gripping port (14a), the inner edge on the side opposite the gripping port (14b) through which the rotary one-way valve (5) is fitted against the main body (3), a tab (15), and the spherical cap (11).

5. The rotary occlusion valve for tracheotomy according to claim 1 characterized in that the rotary one-way valve (5) also contains the one-way membrane comprising a diaphragm (18) and the gripping port (17).

* * * * *